United States Patent [19]

Bajgrowicz et al.

[11] Patent Number: 6,043,210
[45] Date of Patent: Mar. 28, 2000

[54] PREPARATION OF THIAMACROLIDE COMPOUNDS

[75] Inventors: Jerzy A. Bajgrowicz, Zurich; Georg Frater, Winterthur; Philip Kraft, Dübendorf, all of Switzerland

[73] Assignee: Givaudan Roure (International) SA, Vernier-Geneve, Switzerland

[21] Appl. No.: 09/015,816

[22] Filed: Jan. 29, 1998

[30] Foreign Application Priority Data

Feb. 14, 1997 [EP] European Pat. Off. .............. 97102395

[51] Int. Cl.[7] .......................... A61K 7/46; C07D 337/00; C07D 305/00
[52] U.S. Cl. ................... 512/12; 512/8; 512/11; 512/25; 512/26; 549/9; 549/263
[58] Field of Search .................... 512/8, 11, 12, 512/25, 26; 549/263, 9

[56] References Cited

U.S. PATENT DOCUMENTS 2,234,551  3/1941  Collaud .
4,218,379  8/1980  Harris et al. .

FOREIGN PATENT DOCUMENTS 96931  6/1957  Netherlands .

OTHER PUBLICATIONS

I.B. Bersuker, *New J. Chem.* 1991, 15:307–20.
T. Nakamura, *Phosphorus, Sulfur, and Silicon.* 1992, 66:59–65.
E.S. Kaboshina, *Chemical Abstracts* 1967,66:16, No. 068820.
G.A. Olah, et al., *Synthesis* 1981, 142.
S. Fujisaki, et al., *Bull. Chem. Soc. Jpn.* 1985, 58, 2429.
Y. Takeuchi, et al., *Chem. Pharm. Bull.* 1986, 34, 1323.
P. Weyerstahl, *J. prakt. Chem.* 1994, 336, 95.
K.J. Rossiter, *Chem. Rev.* 1996, 96, 3201.
E.T. Theimer, et al.,*J. Agr. Food Chem.* 1967,15(1), 6.
V.N. Belov, et al.,*J. Org. Chem. USSR* (Engl. Transl.) 1965, 1, 539.
H. Matsuyama, et al., *J. Org. Chem.* 1989, 54, 5218.
M. Kolb, et al., *Synth. Commun.* 1981, 11(9), 763.

*Primary Examiner*—Gabrielle Brouillette
*Assistant Examiner*—Monique T. Cole
*Attorney, Agent, or Firm*—Mark E. Waddell; Stephen M. Haracz; Bryan Cave LLP

[57] ABSTRACT

The invention is related to novel thiamacrolides, especially musk odorants, having extremely low threshold values, their use in functional perfumery such as fine perfumery, as well as to the preparation of thiamacrolide compounds.

5 Claims, No Drawings

PREPARATION OF THIAMACROLIDE COMPOUNDS

FIELD OF THE INVENTION

The invention is concerned with novel thiamacrolides, especially musk odorants, having extremely low threshold values, their use in functional perfumery such as fine perfumery, as well as a process for the manufacture of these and analogue compounds.

BACKGROUND OF THE INVENTION

Because of their warm, erogenous-animalic and long-lasting odor, musk odorants number among the compounds which are most used in perfumery. The poor biological degradability, a certain phototoxicity, as well as the suspected neurotoxicity of benzoid musk odorants, has led in recent times to the increased use of macrocyclic compounds, which are derived from naturally occurring musk substances and which are quite safe from an ecological point of view. However, high production costs prevent their use on a large scale.

Macrocycles, which by virtue of their low threshold value could be used in lower concentrations than usual and thereby give rise to lower costs, could provide a solution. Although it is possible to obtain information relating to core structures, and in spite of numerous investigations concerning structure-odor relationships of odorants, such as disclosed in P. Weyerstahl, *J. prakt. Chem.* 1994, 336, 95; K. J. Rossiter, *Chem. Rev.* 1996, 96, 3201, a prediction of the intensity or of the threshold value of macrocycles having a musk odor has hitherto been impossible.

SUMMARY OF THE INVENTION

We have now found a small class of thiamacrolides I, which have extremely low threshold values, namely of 0.1–0.3 ng/l air, i.e. up to 10 times lower than the threshold value of the most frequently used macrolide 15-pentadecanolide (5, 1.1 ng/l). This is all the more surprising, since thiamacrolides have already been the subject of a patent, Naarden, Netherlands Patent No. 96391. The compounds synthesized there have, however, been found to have a much weaker odor than 15-pentadecanolide (5). See E. T. Theimer, J. T. Davies, *J. Agr. Food Chem.* 1967, 15, 8.

DETAILED DESCRIPTION OF THE INVENTION

This novel class of thiamacrolides can be represented by the general formula

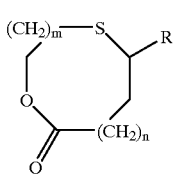

I wherein R=H and wherein m=9 and n=3, or
  m=7 and n=4, or
  m=3 and n=8, or
  m=7 and n=3.

It accordingly embraces the compounds of formulae 1–4.

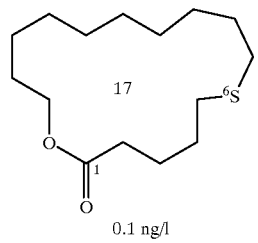

1

0.1 ng/l

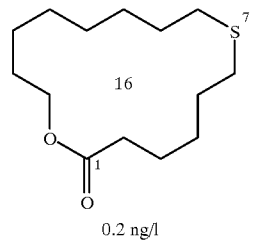

2

0.2 ng/l

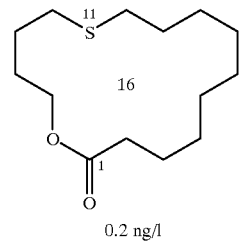

3

0.2 ng/l

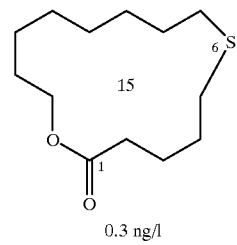

4

0.3 ng/l

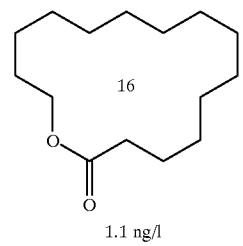

5

1.1 ng/l

In addition to extremely low threshold values the compounds I have a very good adhesion. All have intensive musk notes which are often accompanied by powdery-sweet accents. In contrast to corresponding compounds which do not contain a sulphur atom and analogous unsaturated macrolides, these compounds are also mainly distinguished by warm, green-mossy nuances. This interaction of powdery-sweet and green-mossy elements with a dominant musk note gives an especially fine perfumistic effect in the case of compound 2.

The thiamacrolides I can, in general, be used in the same manner as the known musk odorants. Thus, they harmonize with a large number of natural and also synthetic products which are customarily used in odorant compositions. In particular, they produce interesting effects in the bottom note in combination with woody and amberous accords, patchouli oil as well as cedarwood and sandalwood odorants. The compounds confer elegance and radiance to flowery essential notes.

Some examples of classes of substance which harmonize especially well are:

| | |
|---|---|
| Natural products, such as | tree moss absolute, geranium oil, jasmin absolute, patchouli oil, rose oil, sandalwood oil, vetiverol and ylang-ylang oil etc. |
| alcohols, such as | citronellol, Ebanol ®, geraniol, linalool, phenylethyl alcohol and Sandalore ®, etc. |
| aldehydes and ketones, such as | Florozone ® (3-(4-ethylphenyl)-2,2-dimethypropional), hydroxycitronellal, Iso-E-Super ® (1,2,3,4,5,6,7,8-octahydro-2,3,8,8-tetramethyl-2-octanaphthalene), Isoraldein ®, maltol, methyl cedryl ketone, methylionone and vanillin, etc. |
| ethers and acetals, such as | ambrox, geranyl methyl ether, rose oxide and Spriambrene ® (2', 2',3,7,7-pentamethyl-spiro[bicyclo[4.1.0]heptane-2,5'-[1,3]dioxan]), etc. |
| esters and lactones, such as | Berryflor ®, γ-decalactone and γ-undecalactone, etc. |

The versatility of the thiamacrolides I enables them to be used widely not only in sweet oriental creations, but also in Fougère', 'Chypre' and 'Floral' olfactorily directions. Not only luxury perfumes, but also compositions for cosmetic products, washing agents and similar bulk products are opened up by the low threshold values and the good adhesion.

The compounds of formula I can be used in wide limits which can range in compositions, for example, from about 0.1 wt. % (detergents) to about 40 wt. % (alcoholic solutions). It will, however, be appreciated that these values are not limiting values, since the experienced perfumer can also produce effects with even lower concentrations or can synthesize novel complexes with even higher dosages. The preferred concentrations range from between about 3 wt. % to about 20%. The compositions produced with compounds I can be used for all types of perfumed consumer goods (eau de Cologne, toilet water, extracts, lotions, creams, shampoos, soaps, salves, powders, deodorants, detergents, etc.).

Accordingly, the compounds I can be used in the production of compositions and, as will be evident from the above compilation, a wide range of odorants or odorant mixtures. In the production of such compositions, the odorants or odorant mixtures enumerated above can be used according to methods known to the perfumer, such as, e.g., from W. A. Poucher, Perfumes, Cosmetics, Soaps, 2nd volume., 7th ed. Chapman and Hall, London 1974.

The manufacture of these novel thiamacrolide I, however, would be very expensive if they could be prepared by the process disclosed in Chemische Fabriek Naarden, Netherlands Patent No. 96391, Jun. 29, 1957, since the starting materials ((ω-alkenols) required for this are difficultly accessible, not available commercially and are very cost-intensive. The same is true for the processes disclosed in V. N. Belov, N. P. Solov'eva, T. A. Rudol'fi, I. A. Voronina, *J. Org. Chem. USSR* (Engl. Transl.) 1965, 1, 539; or in H. Matsuyama, T. Nakamura, N. Kamigata, *J. Org. Chem.* 1989, 54, 5218.

Accordingly, the present invention also provides a process for the manufacture of the thiamacrolides I, which is achieved by a novel route which starts from aliphatic diols, as well as lactones 6, as readily accessible starting materials.

The process for preparing the thiamacrolides is set for schematically below. The process begins with a tandem ring opening-esterification reaction of the lactone 6, which is prepared in a manner known per se, with trimethylsilyl iodide and an alcohol R'OH with 1–6 carbon atoms such as disclosed in M. Kolb, J. Barth, *Synth. Commun.* 1981, 11. 763, whereby trimethylsilyl iodide can also be generated in situ, e.g. G. A. Olah, S. C. Narrang, G. F. Salem, B. G. B. Gupta, *Synthesis* 1981, 142.

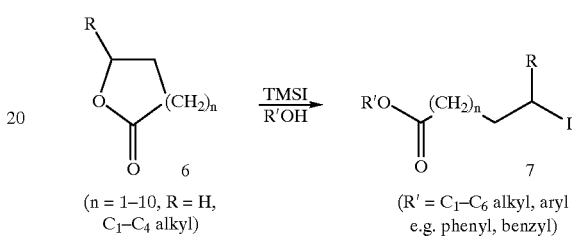

(n = 1–10, R = H, $C_1$–$C_4$ alkyl)       (R' = $C_1$–$C_6$ alkyl, aryl e.g. phenyl, benzyl)

The iodoesters 7 are then in accordance with the invention converted directly into ω-hydroxy-(n+3)-thiacarboxylic acids 11, conveniently in a novel one-pot reaction. In contrast to similar prior art reactions (see, for example, S. Fujisaki, I. Fujiwara, Y. Norisue, S. Kajigaeshi, *Bull. Chem. Soc. Jpn.* 1985, 58, 2429; Y. Takeuchi, K. Sakagawa, M. Kubo, M. Yamato, *Chem. Pharm. Bull.* 1986, 34, 1323), which do not lead to the product 10, in the reaction in accordance with the invention the tetramethylthiouronium salt 8 and the monoalcoholate 9 are conveniently prepared separately from the corresponding diol and then reacted with each other at elevated temperatures, usually under reflux in an aprotic solvent, especially in acetonitrile.

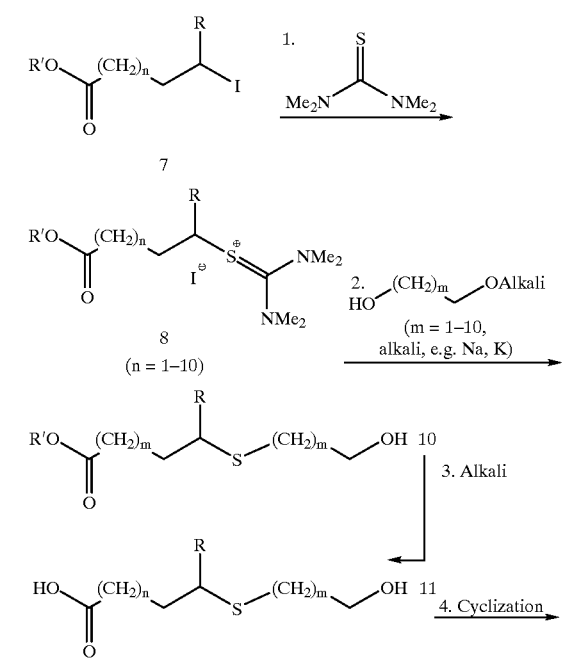

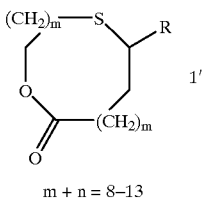

$m + n = 8–13$

The cyclization of the (ω-hydroxy-(n+3)-thiacarboxylic acids 11 (present after the usual basic saponification of the reaction products 10) to thiamacrolides I' takes place without intermediate purification of the hydroxy acids. It is preferably carried out by heating 11 with an entraining agent in the presence of a base as the catalyst, e.g. according to the process of Collaud Givaudan, U.S. Pat. No. 2,234,551. Especially suitable entraining agents are mono- or polyvalent alcohols, for example difficultly volatile alcohols such as glycerol or ethylene glycol, etc. Strong bases, such as potassium methylate or sodium methylate, especially come into consideration as bases employed in the process. Suitable temperatures are reflux temperature under reduced pressure, which lie in the range of from about 100° C. to about 200° C.

The stereochemistry of the compounds of formulae I and I' is determined by the residue (R) of the lactone 6 which is used. Thereby, enantiomerically-enriched and enantiomerically-pure alkyl-substituted thiamacrolides can consequentially be manufactured. The present formulae I and I' accordingly embrace all possible stereoisomers.

In the case of the macrocyclic compounds I' with $R=C_1–C_4$-alkyl suitable as musk odorants, the total sum of carbon atoms should conveniently be n+m+R=14–17 C atoms.

EXAMPLES

The present invention is described further in the following examples which are presented solely for the non-limiting purpose of further illustrating the invention.

Example 1

7-Thia-15-pentadecanolide (2)

Ethyl 6-iodocaproate (7, n=3, R=H, R'=Et): 50 ml (0.37 mol) of trimethylsilyl iodide was added dropwise to a solution of 25 ml (0.24 mol) of ε-caprolactone and 35 ml (0.62 mol) of ethanol in 200 ml of dichloromethane under argon at 0° C. After stirring at room temp. for 1 hr. the reaction mixture was poured into 100 ml of water. The organic phase was washed with 100 ml of water and 100 ml of sat. sodium hydrogen carbonate solution, dried over sodium sulphate and concentrated to dryness on a rotary evaporator. After flash chromatography (n-pentane/MTBE, 9:1, $hR_f$=74) on silica gel 30 g (46%) of ethyl 6-iodocaproate as a colorless liquid was obtained.

15-Hydroxy-7-thiapentadecanoic acid (9, n=3, m=7, R=H): a solution of 14 g (0.11 mol) of tetramethylthiourea and 28 g (0.10 mol) of ethyl 6-iodocaproate in 220 ml of dry acetonitrile was heated under reflux for 2 h. In a further reaction vessel 23 g (0.16 mol) of 1,8-octanediol was dissolved in 650 ml of dry acetonitrile under argon, the solution was treated with 4.5 g (0.11 mol) of a 60 percent sodium hydride suspension in mineral oil and heated under reflux for 45 min. Both batches were left to cool to 50° C. and thereupon combined cautiously within 30 min. The combined reaction mixtures were heated to reflux for 14 h., subsequently saponified with 60 ml of 10 percent potassium hydroxide solution for 3 h. at room temp., concentrated on a rotary evaporator and then added to 1 l of water. The mixture was extracted twice with 500 ml of MTBE each time, and the organic extracts were washed three times with 50 ml of 2N sodium hydroxide solution each time. The aqueous phase was acidified with conc. phosphoric acid and extracted three times with 500 ml of MTBE each time. After drying the combined organic extracts over magnesium sulphate and removing the solvent on a rotary evaporator 22 g of crude 15-hydroxy-7-thiapentadecanoic acid as a yellowish wax-like solid was obtained. An analytical sample was obtained after flash chromatography (MTBE/n-pentane, 2:1, $hR_f$=33) on silica gel.

IR (film): $v$=1691 cm$^{-1}$ (ν C=O), 1064 cm$^{-1}$ (ν C—OH), 1284/1267 cm$^{-1}$ (ν CO—O), 3423/3362 cm$^{-1}$ (ν O—H), 1198 cm$^{-1}$ (δ O—H). —$^1$H-NMR (CDCl$_3$): δ=1.31–1.49 (m, 10H, 4-,10-H$_2$–13-H$_2$), 1.54–1.71 (m, 8H, 2-,5-,9-,14-H$_2$), 2.36 (t, J=7.6 Hz, 2H, 2-H$_2$), 2.50/2.51 (t, J=7.2 Hz, 4H, 6-,8-H$_2$), 3.65 (t, J=6.6 Hz, 2H, 15-H$_2$).—$^{13}$C-NMR (CDCl$_3$): δ=24.18 (t, C-3), 25.46 (t, C-13), 28.12/28.61/28.98 (t, C-4,-10,-11), 29.08/29.13/29.44 (t, C-5,-9,-12), 31.68/31.92 (t, C-6,-8), 32.26 (t, C-14), 33.78 (t, C-2), 62.57 (t, C-15), 178.59 (s, C-1).—MS (EI): m/z (%)=143 (100) (C$_8$H$_{15}$S⊕), 161 (8) (C$_8$H$_{17}$OS⊕), 175 (4) (C$_9$H$_{19}$OS⊕), 229 (5) (C$_{12}$H$_{21}$O$_2$S⊕); 276 (22) (C$_{14}$H$_{28}$O$_3$S⊕).

7-Thia-15-pentadecanolide (2): 22 g of crude 15-hydroxy-7-thiapentadecanoic acid (9, n=3, m=7, R=H) was treated with 0.45 ml (4.0 mmol) of 50 percent potassium hydroxide solution and byproducts were distilled off at 180° C./20–23 mbar for 1 h. Thereupon, the reaction vessel was fitted with a condenser and separator and 1.2 g (17 mmol) of potassium methylate in 300 ml of anhydrous glycerol was added to the reaction mixture. The mixture was heated to reflux at 153° C./4–6 mbar over the separator for 2 d., with 1.2 g (17 mmol) of potassium methylate again being added after 14 h. The separated glycerol was poured into 800 ml of water and the crude product was extracted twice with 500 ml of MTBE each time and once with 500 ml of n-pentane. The combined organic extracts were dried over magnesium sulphate and concentrated to dryness on a rotary evaporator. After flash chromatography (n-pentane/MTBE, 19:1, hRf=46) on silica gel, 2.9 g (11% overall yield) of 7-thiapentadecanolide as a colorless wax-like solid with an intensive, linear musk odor accompanied by green-mossy aspects with a threshold value of 0.2 ng/l air was obtained.

IR (film): $v$=1732 cm$^{-1}$ (ν C=O), 1247 cm$^{-1}$ (ν C—CO—O), 1124 cm$^{-1}$ (ν C—O—C). —$^1$H-NMR (CDCl$_3$): δ=1.26–1.50 (m, 10H, 4-,10-H$_2$–13-H$_2$), 1.56–1.77 (m, 8H 3-,5-,9-,14-H$_2$), 2.35 (t, J=6.8 Hz, 2H, 2-H$_2$), 2.52/2.53 (t, J=6.8 Hz, 4H, 6-,8-H$_2$), 4.15 (t, J=5.2 Hz, 2H, 15-H$_2$).—$^{13}$C-NMR (CDCl$_3$): δ=24.68 (t, C-3), 25.16 (t, C-13), 26.11 (t, C-4), 27.12/27.25/27.58/27.73 (t, C-10,-11,-12,-14), 28.32/28.36 (t, C-5,-9), 30.66/30.92 (t, C-6,-8), 34.36 (t, C-2), 64.01 (t, C-15), 173.65 (s, C-1).—MS (EI): m/z (%)=143 (100) (C$_8$H$_{15}$S⊕), 157 (7) (C$_9$H$_{17}$S⊕), 229 (7) (C$_{12}$H$_{21}$O$_2$S⊕), 258 (74) (C$_{14}$H$_{26}$O$_2$S⊕).

Example 2

4-Methyl-5-thia-15-pentadecanolide (I, n=1, m=9, R=Me)

Ethyl 4-iodovalerate (7, n=1, R=Me, R'=Et): Analogously to the synthesis of ethyl 6-iodocaproate (Example 1), 67 ml (0.96 mol) of γ-valerolactone was reacted with 140 ml (2.4 mol) of ethanol and 200 ml (1.4 mol) of trimethylsilyl iodide. After usual working-up and flash chromatography (n-pentane/MTBE, 9:1, $hR_f$=63) 94 g (73%) of ethyl 4-iodovalerate as a colorless liquid was obtained.

4-Methyl-5-thia-15-pentadecanolide (I, n=1, m=9, R=Me): Analogously to the synthesis of 7-thia-15-pentadecanolide (Example 1) via 15-hydroxy-7 thiapentadecanoic acid, 15 g (0.12 mol) of tetramethylthiourea was reacted with 25 g (0.96 mol) of ethyl 4-iodovalerate in 200 ml of dry acetonitrile and, in parallel, 20 g (0.12 mol) of decanediol in 640 ml of dry acetonitrile was reacted with 5.1 g (0.12 mol) of 60 percent sodium hydride suspension in mineral oil, after which the reaction products were combined as described and heated under reflux for 20 h. After the usual working-up 19 g of crude 15-hydroxy-4-methyl-5-thiapentadecanoic acid were obtained, which was polymerized with 0.07 ml (0.62 mmol) of 50 percent potassium hydroxide solution and depolymerized with two 0.9 g (13 mmol) aliquots of potassium methylate in 300 ml of glycerol as described under Example 1. After usual working-up and flash chromatography, 3.6 g (14% overall yield) of 4-methyl-5-thia-15-pentadecanolide as a colorless wax-like solid having a sweet musk-like odor with green and metallic nuances with a threshold value of 1.8 ng/l air was obtained.

IR (film): ν=1734 cm$^{-1}$ (ν C=O), 1163/1194 cm$^{-1}$ (ν C—O), 1268 cm$^{-1}$ (ν C—CO—O). —$^1$H-NMR (CDCl$_3$): δ=1.28 (d, J=6.8 Hz, 3H, 4-Me), 1.31–1.65 (m, 16H, 7-H$_2$–13-H$_2$), 1.79 (dddd, J=7.2, 6.8, 6.4 and 1.0 Hz, 1H, 3-H$_b$), 1.79 (dddd, J=7.2, 6.8, 6.4 and 1.0 Hz, 1H, 3-H$_b$), 1.89 (dddd, J=7.2, 6.8, 6.8 and 6.4 Hz, 1H, 3-H$_a$), 2.41 (ddd, J=15.6, 6.4 and 6.4 Hz, 1H, 2-H$_b$), 2.49 (ddd, J=12.8, 6.8 and 6.8 Hz, 1H, 6-H$_b$), 2.55 (ddd, J=12.8, 6.8 and 6.8 Hz, 1H, 6-H$_a$), 2.65 (ddd, J=15.6, 7.2 and 7.2 Hz, 1H, 2-H$_a$), 2.80 (qdd, J=6.8, 6.8 and 1.0 Hz, 1H, 4-H), 4.06 (ddd, J=10.8, 6.4 and 3.6 Hz, 1H, 15-H$_b$), 4.23 (ddd, J=10.8, 8.0 and 3.6 Hz, 1H, 15-H$_a$).—$^{13}$C-NMR (CDCl$_3$): δ=21.43 (q, 4-Me), 24.25 (t, C-3), 26.10/26.11/26.20 (t, C-8,-13,-14), 26.69/27.01/27.89/28.11 (t, C-9,-10,-11,-12), 29.17 (t, C-7), 31.43/31.56 (t, C-2,-6), 38.87 (d, C-4), 63.79 (t, C-15), 173.53 (s, C-1).—MS (EI) m/z (%)=87 (100) (C$_4$H$_7$S⊕), 101 (97) (C$_5$H$_9$S⊕), 114 (77) (C$_6$H$_{10}$S⊕), 132 (35) (C$_7$H$_{16}$S⊕), 171 (23) (C$_{10}$H$_{19}$S⊕), 257 (1) (C$_{14}$H$_{25}$O$_2$S⊕), 272 (16) (C$_{15}$H$_{28}$O$_2$S⊕).

The following compounds are accessible in a corresponding manner. Therefore, only the spectroscopic data are set forth for them.

Example 3

6-Thia-16-hexadecanolide (1)

Intensive musk odor with powdery-dry effect with a threshold value of 0.1 ng/l air.—IR (film): ν=1734 cm$^{-1}$ (ν C=O), 1256 cm$^{-1}$ (ν C—CO—O), 1181/1128 cm$^{-1}$ (ν C—O).—$^1$H-NMR (CDCl$_3$): δ=1.32–1.46 (m, 12H, 9-H$_2$–14-H$_2$), 1.56–1.67 (m, 6H, 3-,4-,8-H$_2$), 1.72–1.79 (m, 2H, 15-H$_2$), 2.35 (t, J=7.2 Hz, 2H, 2-H$_2$), 2.51/2.52 (2t, J=7.2 Hz, 4H, 5-,7-H$_2$), 4.15 (dd, J=5.6 and 5.6 Hz, 2H, 16-H$_2$).—$^{13}$C-NMR (CDCl$_3$): δ=24.32 (t, C-3), 25.06 (t, C-14), 26.75/26.92/26.92 (t, C-10,-11,-12), 27.34/27.64 (t, C-9,-13), 28.32/28.46 (t, C-4,-8), 29.79 (t, C-15), 31.61/31.93 (t, C-5,-7), 34.28 (t, C-2), 64.05 (t, C-16), 173.43 (s, C-1).—MS (EI) m/z (%)=87 (100) (C$_4$H$_7$S⊕), 101 (61) (C$_5$H$_9$S⊕), 117 (27) (C$_6$H$_{13}$S⊕), 171 (31) (C$_{10}$H$_{19}$S⊕), 272 (18) (C$_{15}$H$_{28}$O$_2$S⊕).

Example 4

11-Thia-15-pentadecanolide (3)

Intensive musk odor with a note of freshly pressed wax and a characteristic soapy-wax like accent essentially for nitromusk substances with a threshold value of 0.2 ng/l air.—IR (film): ν=1734 cm$^{-1}$ (ν C=O), 1245 cm$^{-1}$ (ν C—CO—O), 1164 cm$^{-1}$ (ν C—O).—$^1$H-NMR (CDCl$_3$): δ=1.34–1.47 (m, 10H, 4-H$_2$–8-H$_2$), 1.58–1.75 (m, 8H, 3-,9-,13-,14-H$_2$), 2.34 (t, J=7.2 Hz, 2H, 2-H$_2$), 2.51/2.52 (2t, J=3.6 Hz, 4H, 10-,12-H$_2$), 4.14 (t, J=4.8 Hz, 2H, 15-H$_2$).—$^{13}$C-NMR (CDCl$_3$): δ=24.65 (t, C-3), 26.14/26.16 (t, C-13,-14), 26.65/26.87 (t, C-4,-8), 27.18/27.59/27.78/28.02 (t, C-5,-6,-7,-9), 30.48/30.86 (t, C-10,-12), 34.17 (t, C-2), 63.64 (t, C-15), 173.79 (t, C-1).—MS (EI) m/z (%)=88 (100) (C$_4$H$_8$S⊕), 101 (14) (C$_5$H$_9$S⊕), 115 (6) (C$_6$H$_{11}$S⊕), 133 (6) (C$_7$H$_{17}$S⊕), 151 (7) (C$_9$H$_{11}$O$_2$⊕), 199 (7) (C$_{11}$H$_{19}$OS⊕), 217 (6) (C$_{11}$H$_{21}$O$_2$S⊕), 258 (10) (C$_{14}$H$_{26}$O$_2$S⊕).

Example 5

6-Thia-14-tetradecanolide (4)

Sweet musk note green-earthy impact with a threshold value of 0.3 ng/l air.—IR (film): ν=1730 cm$^{-1}$ (ν C=O), 1261/1221 cm$^{-1}$ (ν C—CO—O), 1131/1156 cm$^{-1}$ (ν C—O).—$^1$H-NMR (CDCl$_3$): δ=1.38–1.56 (m, 10H, 3-H$_2$, 9-H$_2$–12-H$_2$), 1.63–1.70 (m, 4H, 4-,8-H$_2$), 1.73–1.78 (m, 2H, 13-H$_2$), 2.38 (t, J=6.4 Hz, 2H, 2-H$_2$), 2.50/2.52 (2t, J=7.6/6.4 Hz, 4H, 5-,7-H$_2$), 4.16 (dd, J=5.2 and 4.0 Hz, 2H, 14-H$_2$).—$^{13}$C-NMR (CDCl$_3$): δ=24.53/24.61 (t, C-3,-12), 25.78 (t, C-13), 26.35/26.83 (t, C-10,-11), 28.13/28.16 (t, C-4,-9), 30.51 (t, C-8), 31.85/32.86 (t, C-5,-7), 34.20 (t,C-2), 63.87 (t, C-14), 173.53 (s, C-1).—MS (EI) m/z (%)=87 (100) (C$_4$H$_7$S⊕), 101 (55) (C$_5$H$_9$S⊕), 117 (32) (C$_6$H$_{13}$S⊕), 143 (51) (C$_8$H$_{15}$S⊕), 159 (4) (C$_8$H$_{15}$OS⊕), 215 (2) (C$_{12}$H$_{24}$OS⊕), 244 (21) (C$_{13}$H$_{24}$O$_2$S⊕).

Example 6

Fresh-spicy wood accord, for use in masculine perfume and body care products

| | Parts by weight |
|---|---|
| 7-THIA-15-PENTADECANOLIDE (2) | 50 |
| BENZYL ACETATE EXTRA | 30 |
| GERANYL ACETATE PURE | 50 |
| 2-PENTYLOXYGLYCOLIC ACID ALLYL ESTER | 3 |
| METHYL ANTHRANILATE | 1 |
| BASIL OIL | 10 |
| BERGAMOT OIL | 200 |
| CARBITOL | 20 |
| METHYL-ALPHA-IONONE | 50 |
| CITRUS OIL | 100 |
| COUMARIN CRYST. | 20 |
| DIHYDROMYRCENOL | 100 |
| TARRAGON OIL | 5 |
| EVERNYL | 3 |
| CLOVE FLOWER OIL | 15 |
| METHYL DIHYDROJASMONATE | 50 |
| ISO E SUPER | 50 |
| ISOEUGENOL | 3 |
| LAVANDIN OIL | 100 |
| METHYL CEDRYL KETONE | 60 |
| NUTMEG OIL | 20 |
| PATCHOULI OIL | 30 |
| γ-UNDECALACTONE | 1 |
| PETITGRAIN OIL PARAGUAY | 7 |
| SANDALORE | 20 |
| VANILLIN | 2 |
| | 1000 |

7-Thia-15-pentadecanolide (2) confers to the composition a sweet musk note, additional volume and softness, and underlines the body care aspect of cosmetic articles.

Example 7

Fresh flowery bouquet, suitable for use in soaps and body care products

|  | Parts by weight |
|---|---|
| 11-THIA-15-PENTADECANOLIDE (3) | 50 |
| BENZYL ACETATE EXTRA | 30 |
| L-BORNYL ACETATE EXTRA | 6 |
| LINALYL ACETATE SYNTH. | 80 |
| PARA-TERT.-BUTYLCYCLOHEXYL ACETATE | 100 |
| VERDYL ACETATE | 15 |
| ALPHA-HEXYLCINNAMALDEHYDE | 130 |
| 2-PENTYLOXYGLYCOLIC ACID | 3 |
| CEDARWOOD OIL | 10 |
| DAMASCENONE, 10% DIETHYL PHTHALATE | 5 |
| DIHYDROMYRCENOL | 80 |
| 2,5-DIMETHYL-2-OCTEN-6-ONE | 7 |
| FLORHYDRAL (3-(3-ISOPROPYLPHENYL)-BUTANAL) | 4 |
| GIVESCONE | 10 |
| METHYL DIHYDROJASMONATE | 40 |
| INDOLINE | 4 |
| ISORALDEINE 95 | 100 |
| CITRAL | 5 |
| LINALOOL SYNTH. | 200 |
| NECTARYL | 10 |
| OKOUMAL (2,4-DIMETHYL-2-(1,1,4,4-TETRA-METHYL-TETRALIN-6-YL)-1,3-DIOXOLANE) | 10 |
| TANGERINOL (6,10-DIMETHYL-5,9-UNDECADIEN-ACETIC ACID-2-YL ESTER) | 1 |
| ACETYLCEDRENE | 100 |
|  | 1000 |

The 11-thia-15-pentadecanolide(3) confers to the composition a fine musk note, gives it sweetness and volume and emphasises the skin care character of cosmetic articles.

The above technical expressions can be identified, e.g. on the basis of the monograph Allured Flavor and Fragrance Materials, 1996, Allured Publishing Company, Carol Stream, Ill. (USA).

While the invention has been illustrated and described with respect to illustrative embodiments and modes of practice, it will be apparent to those skilled in the art that various modifications and improvements may be made without departing from the scope and spirit of the invention. Accordingly, the invention is not to be limited by the illustrative embodiments and modes of practice.

We claim:

1. A compound of the formula:

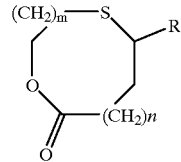

wherein R=H and wherein m=9 and n=2, or
    m=7 and n=3, or
    m=7 and n=2.

2. A compound of claim 1, wherein the compound is 6-Thia-16-hexadecanolide.

3. A compound of claim 1, wherein the compound is 7-Thia-15-pentadecanolide.

4. A compound of claim 1, wherein the compound is 6-Thia-14-tetradecanolide.

5. An odorant composition comprising a compound of formula I in accordance with claim 1.

* * * * *